(12) United States Patent
Takagi et al.

(10) Patent No.: US 6,969,376 B2
(45) Date of Patent: Nov. 29, 2005

(54) SAFETY INDWELLING NEEDLE

(75) Inventors: Hiroshi Takagi, Yokohama (JP);
Kentaro Takemae, Kawasaki (JP)

(73) Assignee: Mitsubishi Pencil Kabushiki Kaisha, Tokyo (JP)

( * ) Notice: Subject to any disclaimer, the term of this patent is extended or adjusted under 35 U.S.C. 154(b) by 132 days.

(21) Appl. No.: 10/088,271

(22) PCT Filed: Jul. 12, 2001

(86) PCT No.: PCT/JP01/06051

§ 371 (c)(1),
(2), (4) Date: Mar. 11, 2002

(87) PCT Pub. No.: WO02/04060

PCT Pub. Date: Jan. 17, 2002

(65) Prior Publication Data

US 2002/0151847 A1   Oct. 17, 2002

(30) Foreign Application Priority Data

Jul. 12, 2000 (JO) .............................. 2000-211726
Nov. 17, 2000 (JP) .............................. 2000-350646

(51) Int. Cl.⁷ ............................ A61M 5/00; A61M 5/32
(52) U.S. Cl. ................. 604/263; 604/164.01; 604/177; 604/198; 604/195; 604/110; 600/585
(58) Field of Search ................. 604/164.08, 177, 604/164.01, 263, 110, 164.05, 585, 171, 158, 604/192–198, 164.12, 161, 508; 600/585

(56) References Cited

U.S. PATENT DOCUMENTS

| 4,747,831 | A | 5/1988 | Kull | |
| 4,850,961 | A | 7/1989 | Wanderer et al. | 604/53 |
| 4,917,669 | A | 4/1990 | Bonaldo | 604/164 |
| 5,520,654 | A | * 5/1996 | Wahlberg | 604/164.08 |
| 5,591,138 | A | * 1/1997 | Vaillancourt | 604/263 |
| 5,891,098 | A | 4/1999 | Huang | 604/164 |
| 6,080,137 | A | 6/2000 | Pike | 604/263 |
| 6,325,781 | B1 | * 12/2001 | Takagi et al. | 604/198 |
| 6,537,253 | B1 | * 3/2003 | Haindl | 604/158 |
| 6,616,631 | B2 | * 9/2003 | Takagi et al. | 604/110 |

FOREIGN PATENT DOCUMENTS

| JP | HEI 3-15481 | 1/1991 | |
| JP | 2000-185096 | 4/2000 | ........... A61M 5/14 |
| JP | 2000-167051 | 6/2000 | |
| JP | 2000-185096 | 7/2000 | |

* cited by examiner

*Primary Examiner*—Nicholas D. Lucchesi
*Assistant Examiner*—Roz Maiorino
(74) *Attorney, Agent, or Firm*—Darby & Darby

(57) ABSTRACT

The mechanism includes: an urging means for urging an inner needle (12) to the side opposite to an outer needle (11) with respect to the axial direction of a holder sleeve (1) for holding the inner needle (12); an actuator (6) which is positioned between the urging means (8) and inner needle (12), moves together with the inner needle (12) and has a puncture position retainer for keeping the inner needle (12) and outer needle (11) ready for puncture and an inner needle retraction actuating portion for allowing for the retraction actuation of the inner needle (12); and a slit (2) for assuring the path of movement of the actuator (6). The puncture position retainer has a puncture position engagement portion whereby the actuator (6) is engaged with the holder sleeve (1) at a position on the outer needle side (11). The inner needle retraction actuating portion includes: an actuating portion (6a) for releasing the actuator (6) from the engaged state of the puncture position engagement portion into the urged state by the urging means (8) and an actuator housing for enclosing the actuator after retraction of the inner needle.

15 Claims, 19 Drawing Sheets

SAFETY INDWELLING NEEDLE

TECHNICAL FIELD

The present invention relates to a technology of a safety indwelling needle comprised of an inner needle which penetrates the skin and reaches a blood vessel and a soft outer needle which is located outside of the inner needle and is to be placed within the blood vessel.

BACKGROUND ART

As a known method for infusing a medical fluid or the like into a patient, an outer needle (catheter) is inserted and placed in the human body to infuse the fluid thereinto. As a device for insertion of the outer needle, indwelling needles have been known to insert and place the outer needle using the inner needle incorporated inside the outer needle.

The inner needle is discarded after placement of the outer needle, but it takes a certain time before it is discarded. Therefore, as to an indwelling needle without a safety mechanism, there is a risk of the inner needle, after use, pricking the human body again during this period or a so-called needlestick accident occurring. Since, in this case, the inner needle might be contaminated with the HIV virus or the like, even a needlestick accident alone has been regarded as a cause of virus infection.

In order to solve this problem, many types of safety indwelling needles which avoid a needlestick accident by confining the inner needle immediately after use have been developed. For example, a technology disclosed in Japanese Patent Application Laid-Open Hei 3 No.15481 is directed to a cannula inserting device for retracting a needle hub, which might cause a needlestick, into a hollow handle by means of an urging means.

Alternatively, Japanese Patent Application Laid-Open No.2000-167051, etc. presented a technology relating to a safety indwelling needle (puncture device) having a retracting mechanism for retracting the inner needle immediately after use into the holder sleeve. These technologies present techniques whereby the inner needle is retracted by means of an urging means when an actuator is operated in a peripheral direction of the holder sleeve so that the actuator is fixed to cutout formed in the holder sleeve.

Since the device disclosed in Japanese Patent Application Laid-Open Hei 3 No.15481 employs a compression spring as the urging means, the outer and inner needles should be assembled by passing them through the interior of the compression spring. Hence extra steps are needed in order for the needle tip not to come into contact with the inner side of the compression spring.

With the safety indwelling needle, disclosed in Japanese Patent Application Laid-Open No.2000-167051, etc., in order to prevent the inner needle once retracted, from being re-exposed, the actuating element (actuating portion) needs to be moved in the peripheral direction so that the actuating element (actuating portion) will be fixed to the cutout (engaging window) formed in the holder sleeve (outer sleeve) In this case, the following problems will occur. First, the handedness problem, whereby the actuation is hard to make depending on the left or right handedness. Further, since one more action needs to be made to fix the actuating element after retraction of the inner needle (needle portion), this disturbs the quick prevention against re-exposure of the inner needle (needle portion). Thus, there have been some problems with prevention against re-exposure of the inner needle (needle portion). Further, since the actuating element (actuating portion) is exposed outside the holder sleeve (outer sleeve), there has been a risk of the actuating element (actuating portion) coming away from the cutout (engagement window) due to an external force so as to cause an event of the inner needle (needle portion) being exposed.

It is therefore an object of the present applicant to provide a technology for a safety indwelling needle which is easy to assemble and prevents the inner needle from being re-exposed by an external force.

Particularly, the object of the inventions described in the first to fifth features is to provide a safety indwelling needle which can prevent the inner needle from being re-exposed by an external force.

DISCLOSURE OF INVENTION

In order to attain the above objects, the present invention has the following configurations.

The first feature of the present invention is directed to a safety indwelling needle, comprised of a metallic inner needle (12) which pierces the skin of a patient and reaches a blood vessel; and a soft outer needle (11) which is located outside the inner needle (12) and placed within the blood vessel. The safety indwelling needle includes a holder sleeve (1) having a retracting mechanism which can hold the inner needle (12) after puncture, from the proximal end to the distal end thereof and does not hold the outer needle (11). The retracting mechanism includes: an urging means for urging the inner needle (12) to the side opposite to the outer needle (11) with respect to the axial direction of the holder sleeve (1); an actuator (6) which moves together with the inner needle (12) when it is withdrawn and has a puncture position retainer for keeping the inner needle (12) and outer needle (11) ready for puncture and an inner needle retraction actuating portion for allowing for the retraction actuation of the inner needle (12); and a slit (2) formed in the holder sleeve (1) for assuring the path of movement of the actuator (6). The puncture position retainer has a puncture position engagement portion whereby the actuator (6) is engaged with the holder sleeve (1) at a position on the outer needle side (11). The inner needle retraction actuating portion includes: an actuating portion (6a) for releasing the actuator (6) from the engaged state of the puncture position engagement portion into the urged state by the urging means (8) and an actuator housing for enclosing the actuator after retraction of the inner needle.

The 'inner needle (12)' is usually a metal, mostly made of stainless steel. The tip of the inner needle (12) is beveled in order to facilitate puncture.

The 'outer needle (11) is placed into the human body after puncture and usually formed of a flexible resin.

The holder sleeve (1) is usually formed of a translucent resin or the like. When the inner needle (12) is punctured into the human body, the blood passes through the inner needle (12) and reaches the proximal portion (inner needle hub 12a) of the inner needle (12). Formation of these portions with a translucent material allows for confirmation of the blood reaching the proximal end of the inner needle (12), hence makes possible visual recognition that the inner needle (12) has reached a blood vessel.

With concern to the retracting mechanism, the structure 'which can hold the inner needle (12) after puncture and does not hold the outer needle (11)' can be achieved when, for example, the inner diameter of the holder sleeve is set greater than the proximal end of the inner needle (12)

(usually, 'inner needle hub (12a)') and set smaller than the proximal end of the outer needle (11)(usually, 'outer needle hub (11a)').

As the 'urging means', string-like rubber, etc., may be employed other than the coil spring which contracts when no load is applied, (The Operation of the First Feature)

First, the inner needle (12) and outer needle (11) is kept ready for puncture by the puncture position engagement portion at which the actuator (6) is engaged with the holder sleeve (1) on the outer needle (11) side. In this position, the inner needle (12) and outer needle (11) are punctured into the skin of a patient.

When the inner needle (12) has reached a blood vessel, the flow of blood through the blood vessel is stopped by one hand while the holder sleeve (1) on the other hand is pulled away from the patient so as to withdraw the inner needle (12) from the blood vessel. The retracting mechanism which can hold the inner needle (12) and does not hold the outer needle (11) is actuated to function as follows.

First, the actuating portion (6a) is operated so as to release the actuator (6) from the engaged state at the puncture position engagement portion. In response to this, the inner needle (12) is urged to the side opposite to the outer needle (11) with respect to the axial direction of the holder sleeve (1) by the urging means (8), so that the actuator (6) moves along the slit (2), which is followed by the inner needle (12). On the contrary, the outer needle (11) will not retract into the holder sleeve (1) but remains at the set position, providing other functions such as being connected to an infusion tube.

The inner needle (12) having been moved to the side opposite to the outer needle of the holder sleeve (1) is held from the proximal to the distal ends, within the holder sleeve (1). Therefore, inner needle (12) having been used for puncture into a patient will not be exposed from the holder sleeve (1), whereby it is possible to prevent occurrence of needlestick injuries.

Since the actuator (6) moves together with the inner needle (12), there would be a risk of the inner needle (12) being exposed from the holder sleeve (1) if an external force causing the actuator (6) to move to the outer needle (11) side is applied after retraction of the inner needle (12). However, since the actuator (6) after storage of the inner needle (12) is enclosed by the actuator housing, there is no risk of an external force acting on the actuator (6) after retraction of the inner needle (12). Accordingly, the inner needle (12) will never be exposed from the holder sleeve (1) due to this cause.

With concern to 'urging means', use of an urging means which contracts when no load is applied enables easier assembly compared to the case where an urging means which extends when no load is applied is used because the inner needle can be assembled without bringing its needle tip into contact with the inner side of the compression spring when it is assembled.

'Actuator housing' should not be limited to the configuration with wall portions and a protective cover as will be described in the feature of the invention, but any configuration will be included in the present invention as long as it prevents external force from acting on the actuating element. For example, the portion on the side opposite to the outer needle (11) in holder sleeve (1) may be formed so as to have an accommodation space for actuator (6) as well.

The second feature of the present invention is the limitation of the safety indwelling needle written in the first feature, and is directed to a safety indwelling needle wherein the actuator housing portion is constructed of wall portions (1b) standing at both sides of the slit (2) in the holder sleeve (1) on the side opposite to the outer needle (11) and a protective cover portion (1c) joining the edges of the wall portions (1b).

The 'wall portions (1b) and a protective cover portion (1c)' may be continuously formed as a seamless part or may be formed as separate parts.

The wall portions may be formed integrally with the holder sleeve (1) as illustrated for the embodiment, or may be formed by discrete projections or the like. It is possible to attain the object of the present invention or produce the effect of preventing the inner needle after use from being exposed if the wall portions are formed to be higher at a certain point, like the apex of a triangle, than the height of the actuator (6). However, to be more effective, it is preferred that the projected parts are high enough across the full-length of the actuating element.

The protective cover is provided so as to cover the top face of the actuating portion (6a) projected through the slit (2) of the holder sleeve (1). Also in this case, the top face of the actuating element is covered, so that it is possible to prevent the inner needle from being re-exposed when the health care worker's palms and the like touch the actuating portion. Accordingly, the encased state of the inner needle can be reliably kept within the interior space of the holder sleeve. As a preferred configuration, the top of the actuating element should be covered when the inner needle is stored in the holder sleeve. This configuration makes the aforementioned effect possible while minimizing the amount of material, etc.

(The Operation of the Second Feature)

Since the actuating portion (6a) after retraction of the inner needle (12) is housed by the walls and protective cover portion, there is no concern of an external force acting on the actuating portion (6a) after retraction of the inner needle (12). Therefore, the inner needle (12) will never be exposed from the holder sleeve (1) due to this cause.

The third feature of the present invention is the limitation of the safety indwelling needle written in the second feature, and is directed to a safety indwelling needle wherein protective cover portion 1c is formed so as to function as a tail plug (1d) for closing the opening of the holder sleeve (1) on the side opposite to the outer needle (11).

(The Operation of the Third Feature)

Since protective cover portion 1c is formed so as to function as a tail plug (1d) for closing the opening of the holder sleeve (1) on the side opposite to the outer needle (11), it is possible to reduce the number of parts and facilitate assembly, hence leading to improvement of the production efficiency.

The fourth feature of the present invention is the limitation of the safety indwelling needle written in any one of the first to third features, and is directed to a safety indwelling needle, wherein the retracting mechanism has a stopper for stopping the inner needle (12) when moved to the rear side with respect to the axial direction of the holder sleeve (1), the stopper includes arrest engagements (1e) for stopping the inner needle (12) stored in the holder sleeve (1) relative to the holder sleeve (1).

When the function of the stopper is provided by the urging means (8) only, no elements other than the urging means (8) are needed. Though the function can be achieved by the urging means (8) only, the engagement arrangement between the holder sleeve (1) and actuator (6) may be provided subsidiarily. Moreover, since the stopper is to reduce the risk of the health care worker erroneously handling the actuating portion (6a) after retraction of the inner needle (12), the function becomes more subsidiary when the actuator housing (1a) is provided.

The arrest engagements, as will be limited by the embodiments described hereinbelow, may be configured so that inner needle hub (12a) and holding sleeve (1) will be engaged with each other, other than the configuration where the arrest engagements (1e) are provided at the position close to the rear end of the slit (2) of the holder sleeve (1) and in the actuating portion (6a).

(The Operation of the Fourth Feature)

The stopper stops the motion of the inner needle (12) having been moved to the side of holder sleeve (1) opposite to the outer needle, by engagement between arrest engagements (1e) for stopping the inner needle (12) held in the holder sleeve (1) relative to the holder sleeve (1). Therefore, there is little risk of the inner needle (12), once moved to the side of holder sleeve (1) opposite to the outer needle, being re-exposed due to an erroneous operation, and the like.

The fifth feature of the present invention is the limitation of the safety indwelling needle written in any one of the first to fourth features, and is directed to a safety indwelling needle, wherein, on the outer needle (11) side of the holder sleeve (1), a grip portion (1g) to be held when the outer needle (11) and inner needle (12) are punctured into the skin of a patient is formed at a position other than the position where the actuating portion (6a) of the actuator (6) is arranged.

(The Operation of the Fifth Feature)

Since the grip portion (1g) is formed at a position other than the position where the actuating portion (6a) of the actuator (6) is arranged, it is possible to reduce the risk of the actuating portion (6a) being erroneously handled when the outer needle (11) and inner needle (12) are punctured into the skin of a patient.

The sixth feature of the present invention is the limitation of the safety indwelling needle written in any one of the first to fifth features, and is directed to a safety indwelling needle further comprising a cap 20 which covers the outer needle (11) and inner needle (12) while keeping them ready for puncture and disables the function of the actuating portion (6a).

(The Operation of the Sixth Feature)

Cap (20) is covered in the state where the outer needle (11) and inner needle (12) are kept ready for puncture. Therefore, the device can be used immediately when the cap (20) is removed just before the use for a patient.

Since the actuating portion (6a) is made disabled when the cap (20) is fitted, it is possible to prevent erroneous operations such as causing withdrawal of inner needle (12) into holder sleeve (1).

The seventh feature of the present invention is also directed to a safety indwelling needle, comprised of a metallic inner needle (12) which pierces the skin of a patient and reaches a blood vessel; and a soft outer needle (11) which is located outside the inner needle (12) and placed within the blood vessel.

First, this safety indwelling needle includes: a holder sleeve (1) having a retracting mechanism which can hold the inner needle (12) after puncture, from the proximal to distal ends thereof and does not hold the outer needle (11). The retracting mechanism includes: a coil spring (8) for urging the inner needle (12) to the side opposite to the outer needle (11) with respect to the axial direction of the holder sleeve (1); an actuator (6) which is arranged between the coil spring (8) and the inner needle (12), moves together with the inner needle (12) when it is withdrawn and has a puncture position retainer for keeping the inner needle (12) and outer needle (11) ready for puncture and an inner needle retraction actuating portion for allowing for the withdrawal actuation of the inner needle (12); and a slit (2) formed in the holder sleeve (1) for assuring the movement path of the actuator (6); an actuator housing for enclosing the actuator (6) after retraction of the inner needle (12); and a stopper for stopping the inner needle (12), having been moved to the side opposite to the outer needle of the holder sleeve (1).

The puncture position retainer has a puncture position engagement portion whereby the actuator (6) is engaged with the holder sleeve (1) at a position on the outer needle (11) side and the engagement can be released.

The inner needle retraction actuating portion includes: an actuating portion (6a) for releasing the actuator (6) from the engaged state of the puncture position engagement portion into the urged state by the coil spring (8).

The actuator housing portion is constructed of wall portions (1b) standing at both sides of the slit (2) in the holder sleeve (1) on the side opposite to the outer needle and a protective cover portion (1c) joining the edges of the wall portions (1b), the protective cover portion (1c) being formed so as to function as a tail plug (1d) for closing the opening of the holder sleeve (1) on the side opposite to the outer needle (11).

The stopper includes arrest engagements (1e) for stopping the inner needle (12) held in the holder sleeve (1) relative to the holder sleeve (1).

BEST MODE FOR CARRYING OUT THE INVENTION (The First Embodiment)

The first embodiment will be described with reference to FIGS. 1 through 8.

Figure 1:
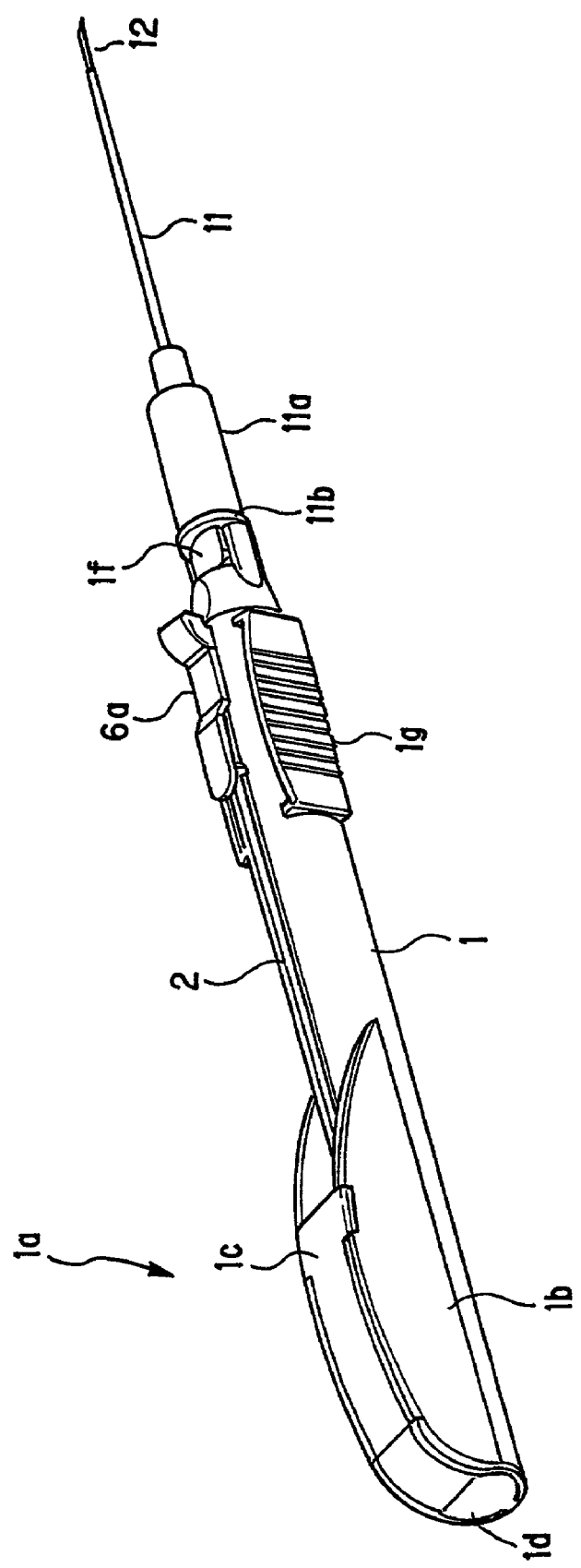
FIG. 1 is an overall perspective view showing an example of a safety indwelling needle of the present invention.
Figure 2:
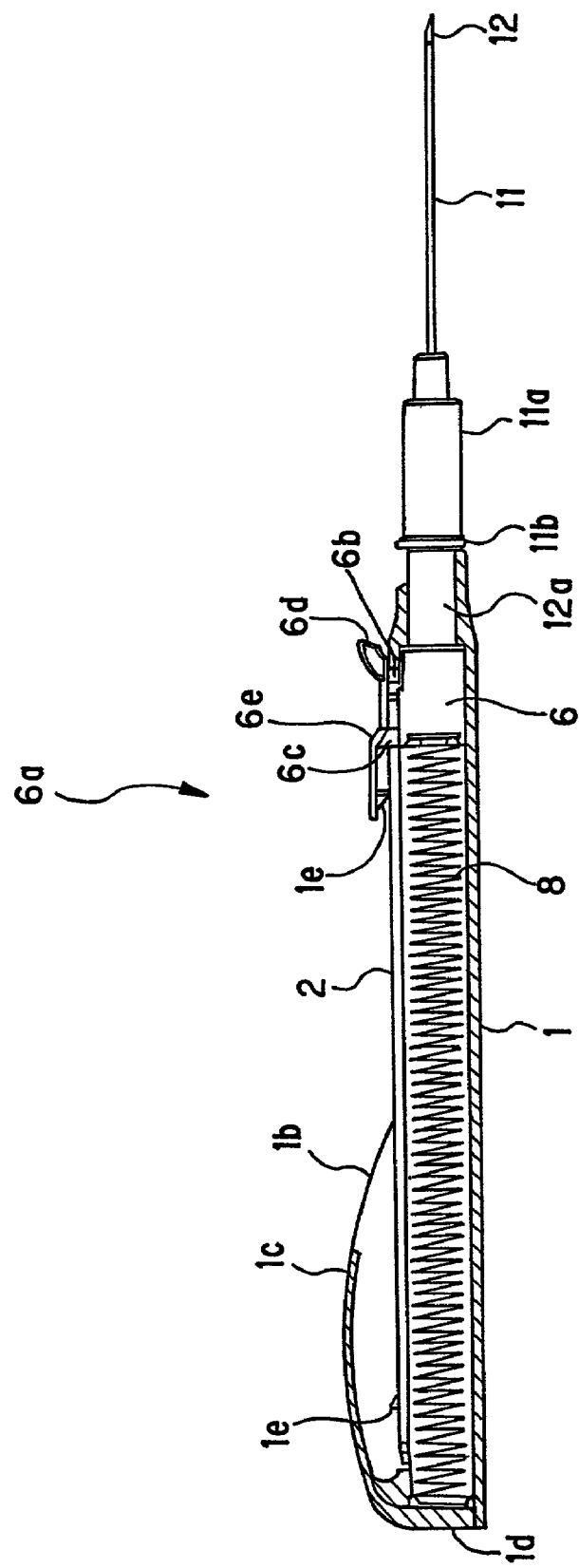
FIG. 2 is a partially sectional vertical view showing a safety indwelling needle before use, according to the present invention.

FIG. 1 shows a safety indwelling needle comprised of a metallic inner needle 12 which penetrates the skin of a patient and reaches a blood vessel and a soft outer needle 11 which is located outside the inner needle 12 and is to be placed within the blood vessel. This safety indwelling needle includes a holder sleeve 1 having a retracting mechanism which can hold the inner needle 12 after puncture, from the proximal to distal ends thereof and does not hold outer needle 11. This retracting mechanism is comprised of an urging means 8 for urging inner needle 12 to the side opposite to outer needle 11 with respect to the axial direction of holder sleeve 1, an actuator 6 located between urging means 8 and inner needle 12 and fixed to urging means 8 and an inner needle hub 12a, a slit 2 formed in holder sleeve 1 for assuring the path of movement of the actuator 6 and a stopper for arresting inner needle 12 which have been moved to the axially rear side of holder sleeve 1 (the side opposite to the outer needle).

As urging means 8, a coil spring which contracts when no load is applied is employed. Use of an urging means which contracts when no load is applied enables easier assembly compared to the case where an urging means which extends when no load is applied is used because the needle tip of the inner needle can be kept out of contact with the inner side of the compression spring when it is assembled.

Figure 6:
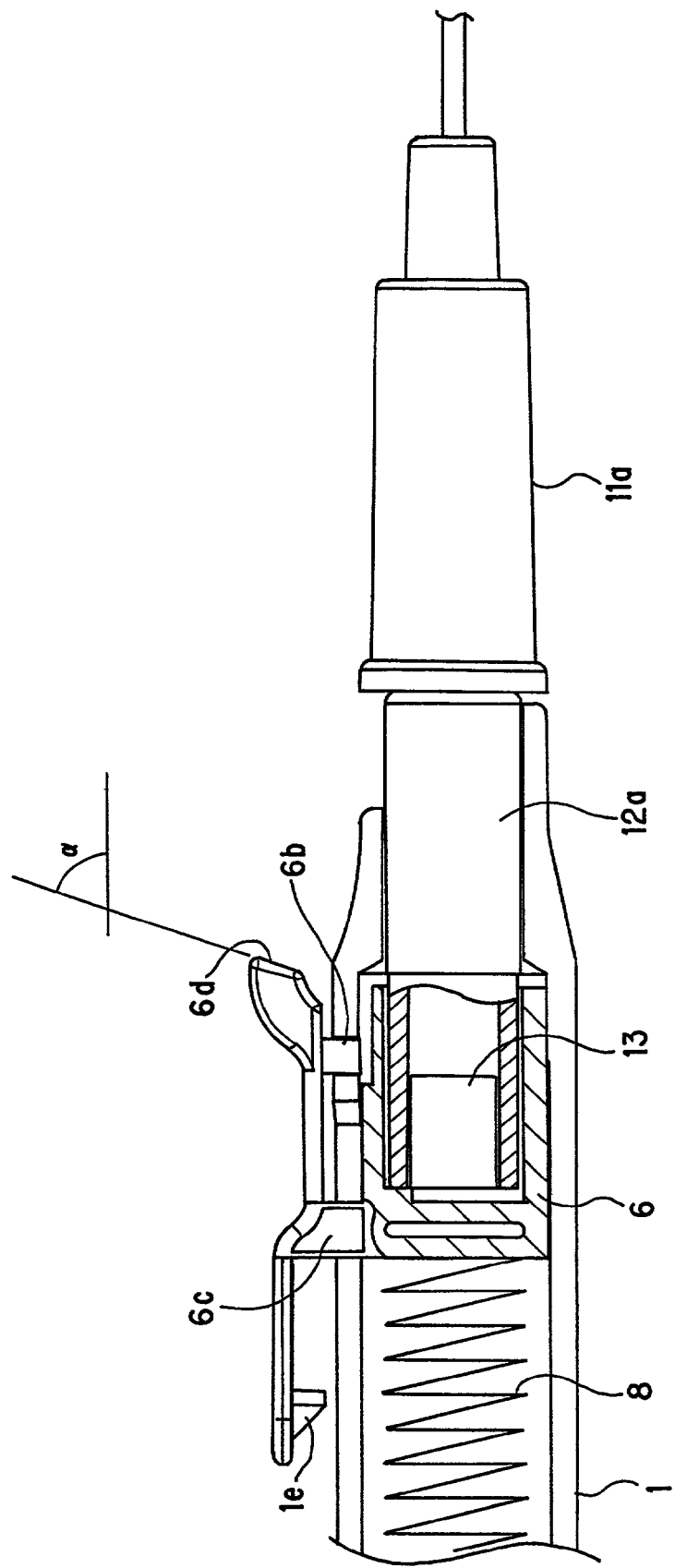
FIG. 6 is an enlarged, partially sectional view showing an actuating portion and thereabout according to the first embodiment.

In order to facilitate connection of an outer needle hub 11a with a tube for medical liquids, the outer needle hub is funnel-shaped having a flange 11b at its rear end. As shown in FIG. 6, a filter 13 is attached inside inner needle hub 12a in order for the patient's blood not to leak out.

Holder sleeve 1 is comprised of an actuator housing 1a for protecting an actuating portion 6a of actuator 6 when inner needle 12 has been retracted in holder sleeve 1, a cutout portion. If formed at the side thereof close to outer needle 11, holding portions 1g to enable the safety indwelling needle body to be held with the first and third digits when inner needle 12 and outer needle 11 are punctured into the patient. Cutout portion if is formed so that the second digit can touch inner needle hub 12a, in order to facilitate operation when inner needle 12 and outer needle 11 are punctured into a patient.

The aforementioned actuator housing 1a is placed the side opposite to outer needle 11 on holder sleeve 1 and is constructed by a pair of wall portions 1b intervening slit 2 between them formed continuously from holder sleeve 1 and a protective cover portion 1c bridging between the wall portions 1b. The wall portion 1b is formed with a curved outline so as to visually suppress the projective appearance of the housing of actuator 6.

Protective cover portion 1c is formed separately from holder sleeve 1 and is formed together with a tail plug 1d which closes the opening of holder sleeve 1 on the side opposite to outer needle 11 and fixes one end of coil spring 8 thereto. Since protective cover portion 1c is formed with tail plug 1d for closing the opening of holder sleeve 1 on the side opposite to outer needle 11, it is possible to reduce the number of parts and facilitate assembly, hence also improve the production efficiency. Fixture of protective cover portion 1c to holder sleeve 1 may be performed by press-fitting, heat-bonding, bonding using adhesives or the like.

Further, protective cover portion 1c has an arrest engagement 1e therein for holding inner needle 12 at the rear end of holder sleeve 1 when the needle has been retracted within holder sleeve 1.

Actuator 6 moves together with inner needle 12 when the needle is retracted and has the following configuration in order to keep inner and outer needles 12 and 11 ready for puncture. First, actuator 6 is comprised of actuating portion 6a projected outward of holder sleeve 1 through slit 2, an insert projection 6b which is inserted to an engagement window 3 formed in holder sleeve 1 on the side close to outer needle 11 to keep actuator 6 to the side close to outer needle 11 opposing the urging force of urging means 8, a lifting portion 6d to which the finger is applied when the insert projection 6b is raised from engagement window 3, an actuating support 6c serving as a fulcrum for the lifting portion 6d and an arrest engagement 1e for holding inner needle 12 at the rear end of holder sleeve 1 when the needle has been retracted within holder sleeve 1. Insert projection 6b and engagement window 3 are formed at such positions that the path of movement of actuating portion 6a is included within the same plane that includes the axis of holder sleeve 1.

When the holding portions 1g, arranged at the front part of holder sleeve 1 on both sides of engagement window 3, are held horizontally by the first and third digits with the second digit set perpendicularly at a position slightly forward with respect to the first and third digits, the rear end of holder sleeve 1 abuts the palm, so that the needle tip can be fixedly held. In this position, inner needle 12 and outer needle 11 are punctured into the vein or any other blood vessel of the human body, then the flange 11b and thereabout at the rear end of outer needle hub 11a is pushed out by the second digit so as to place the outer needle 11 into the blood vessel. Since cutout if is formed at the front most end of holder sleeve 1, flange 11b and thereabout are adapted to be easily pushed out.

Since inner needle 12 is unsheathed after outer needle 11 has been placed into the patient, lifting portion 6d at the front part of actuating portion 6a is lifted upward so as to release the inner needle from the engagement. At this moment, the path of movement of lifting portion 6d is not a rotational motion direction about axis of holder sleeve 1, so no handedness problem will occur. As pulled by coil spring 8 fixed between tail plug 1d and actuator 6, actuator 6 is moved backwards into holder sleeve 1. Since inner needle 12 is fixed to actuator 6 via inner needle hub 12a, inner needle 12 is also pulled into holder sleeve 1. In this way, inner needle 12 is kept away from the outside, thus enabling safe disposal.

Figure 3:
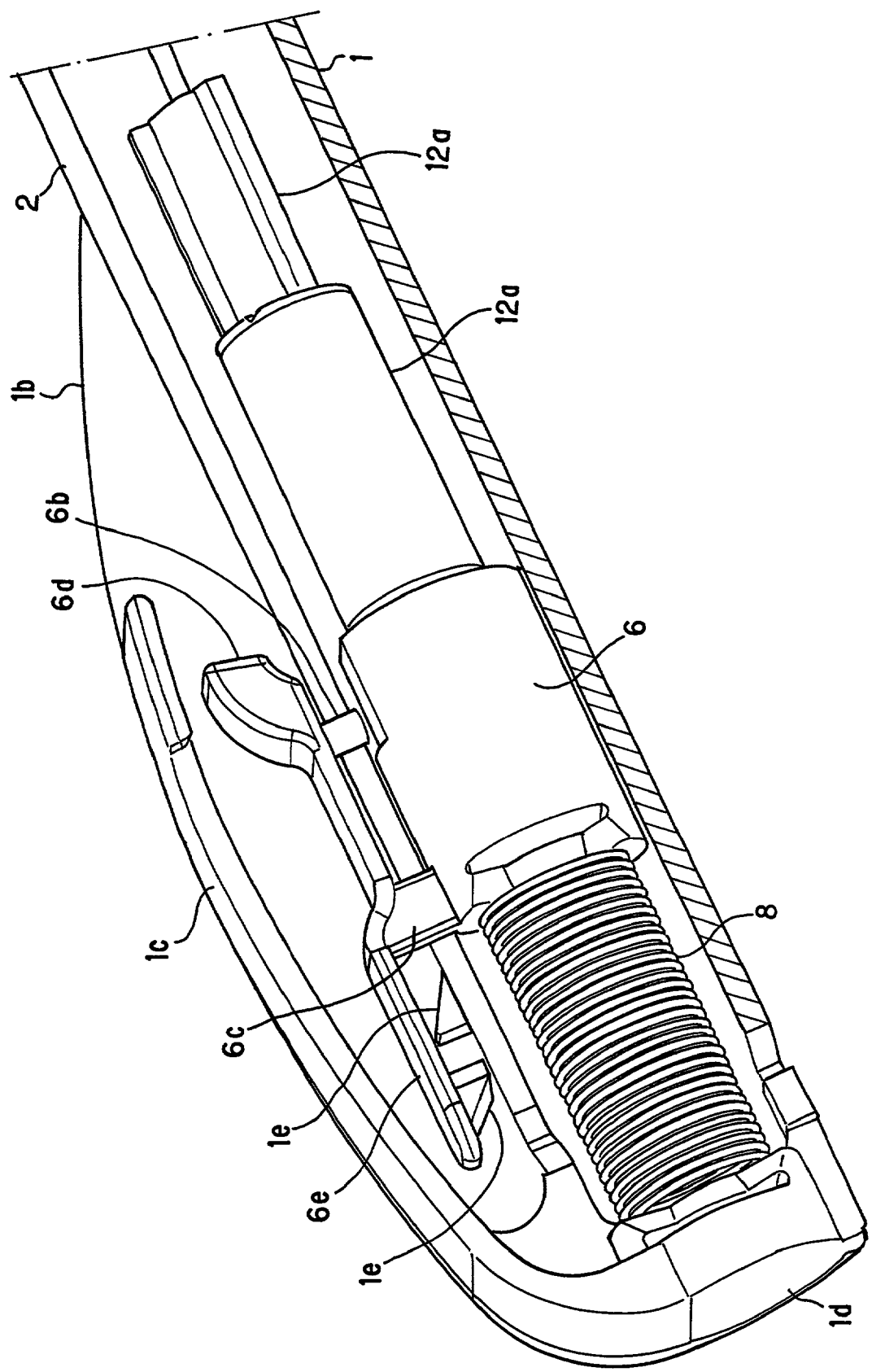
FIG. 3 is a partly enlarged, partially sectional vertical view showing a configurational example of an actuator housing and thereabout when the inner needle is retracted into a holder sleeve.

As shown in FIG. 3, actuating portion 6a projected from holder sleeve 1 is covered over its top face 6e by a protective cover 1c and enclosed by walls 1b formed continuously from holder sleeve 1 on both sides of actuating portion 6a. Each of these elements is kept away at a large enough clearance from actuating portion 6a so that there is little risk of actuating portion 6a being externally pressed by the palm or the like of the health care worker.

Triangular arrest engagements 1e are formed on actuating portion 6a and at around the rear end of slit 2, respectively. The arrest engagement 1e formed at the rear of actuating portion 6a which has been moved by the urging force of coil spring 8 will readily pass over the arrest engagement 1e of holder sleeve 1. Since two arrest engagements 1e have interlocking shapes with each other or since the opposing sides of the triangles of actuating portion 6a and holder sleeve 1 are right-angled to the respective portions, the movement of actuator 6 toward the side of outer needle 11 is restrained. As a result, the forward movement of inner needle 12 is also restrained.

Figure 4:
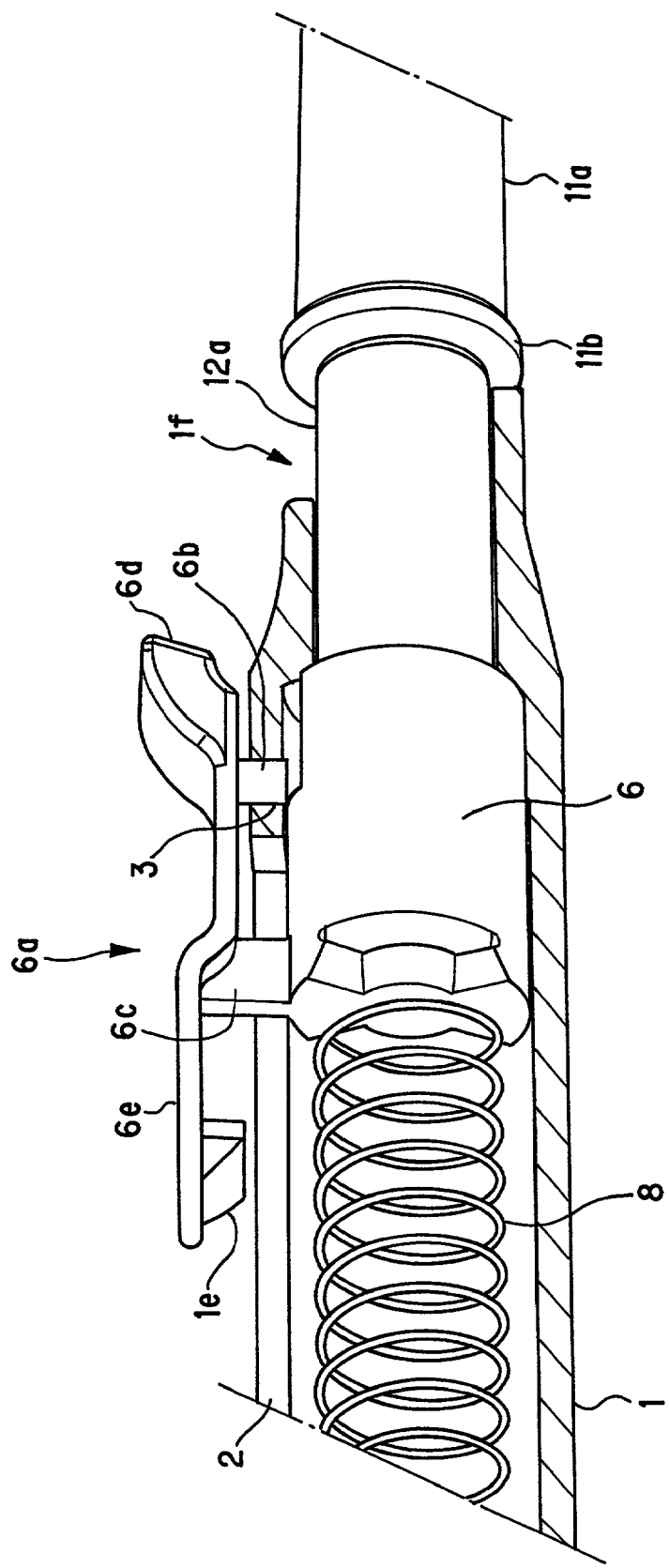
FIG. 4 is a partly enlarged, partially sectional vertical view showing the actuating portion and thereabout shown in FIG. 1.

FIG. 4 shows a state before puncture into a patient. Before inner and outer needles 12 and 11 are punctured into a blood vessel, insert projection 6b of actuating portion 6a has been set in engagement window 3 of holder sleeve 1. This opposes the urging force of coil spring 8 which tends to urge inner needle 12 into holder sleeve 1.

In order to retract inner needle 12 into holder sleeve 1 after outer needle 11 has been placed into the human body, the lifting portion 6d of actuating portion 6a is pulled upwards. Then actuating portion 6a rises at the front end, pivoting on actuating support 6c, so that insert projection 6b which has been fitted in engagement window 3 is pulled out. Resultantly, inner needle 12 together with actuator 6 is retracted into holder sleeve 1 by the urging force of coil spring 8.

Figure 5:
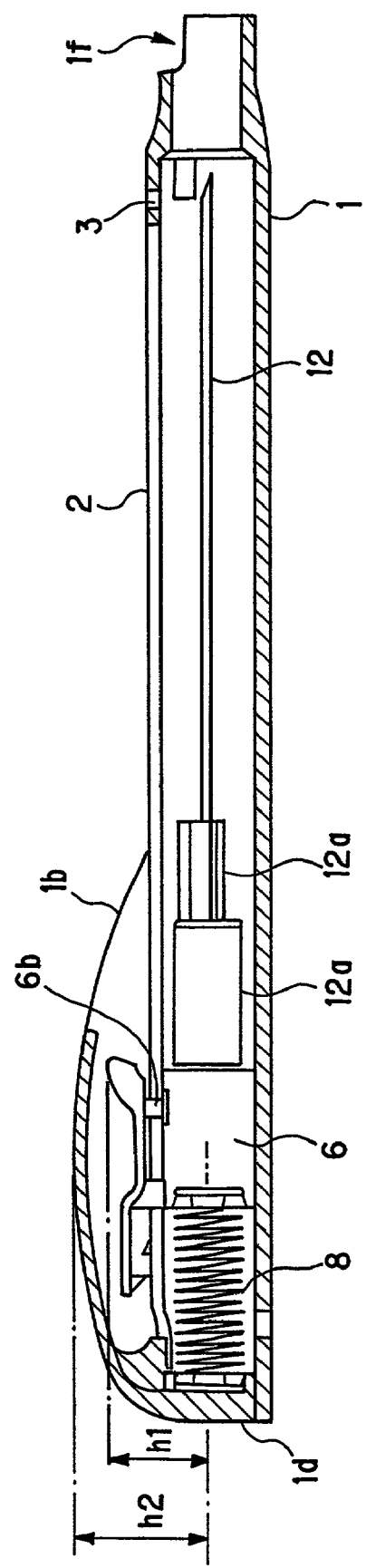
FIG. 5 is a partially sectional vertical view showing a safety indwelling needle when the inner needle is retracted into the holder sleeve.

FIG. 5 shows the fact that the actuating element 6 is difficult to be interfered with from an external since the height h2 of wall portions 1b is greater than the height h1 of actuating element 6. In the present embodiment, h1 and h2 are set at about 7.3 mm and 9.7 mm, respectively.

Figure 7:
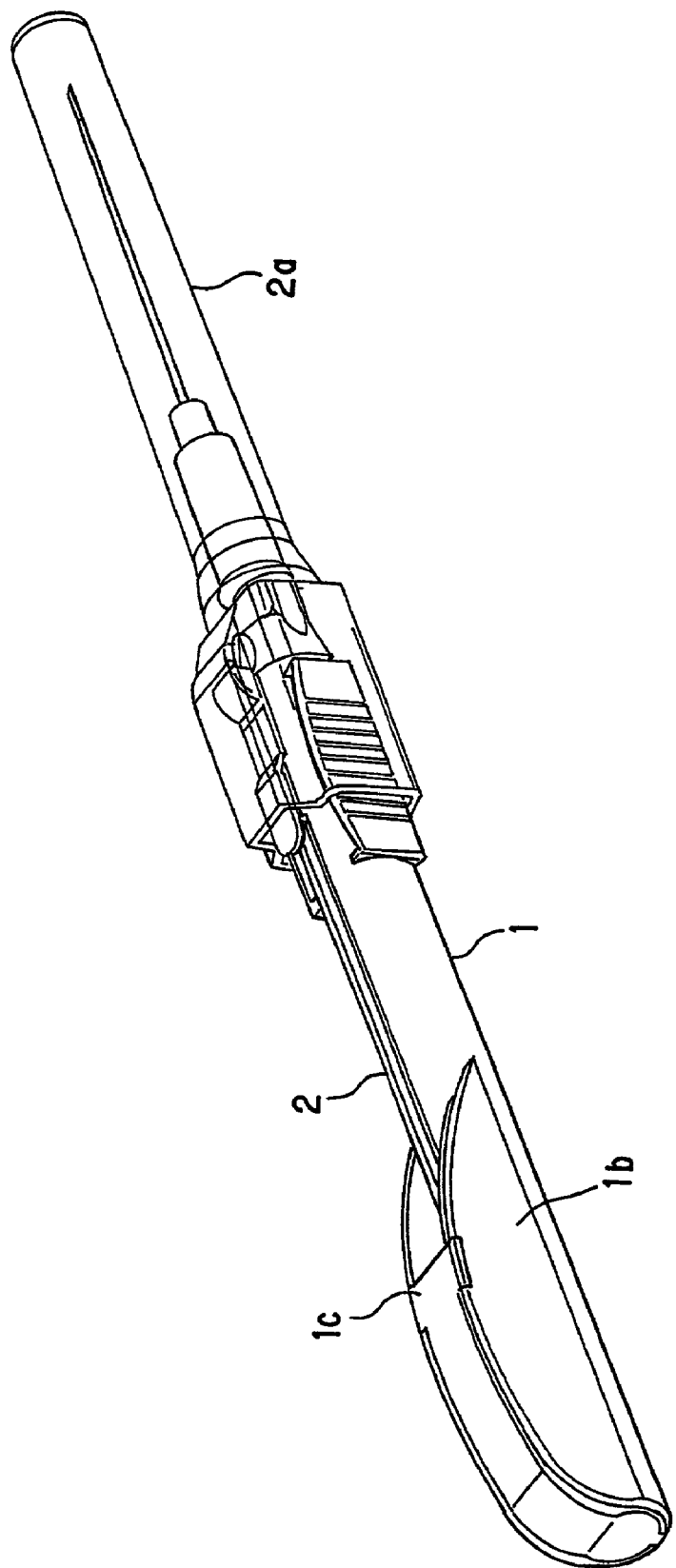
FIG. 7 is an overall perspective view showing an example of a safety indwelling needle with a cap fitted thereto.
Figure 8:
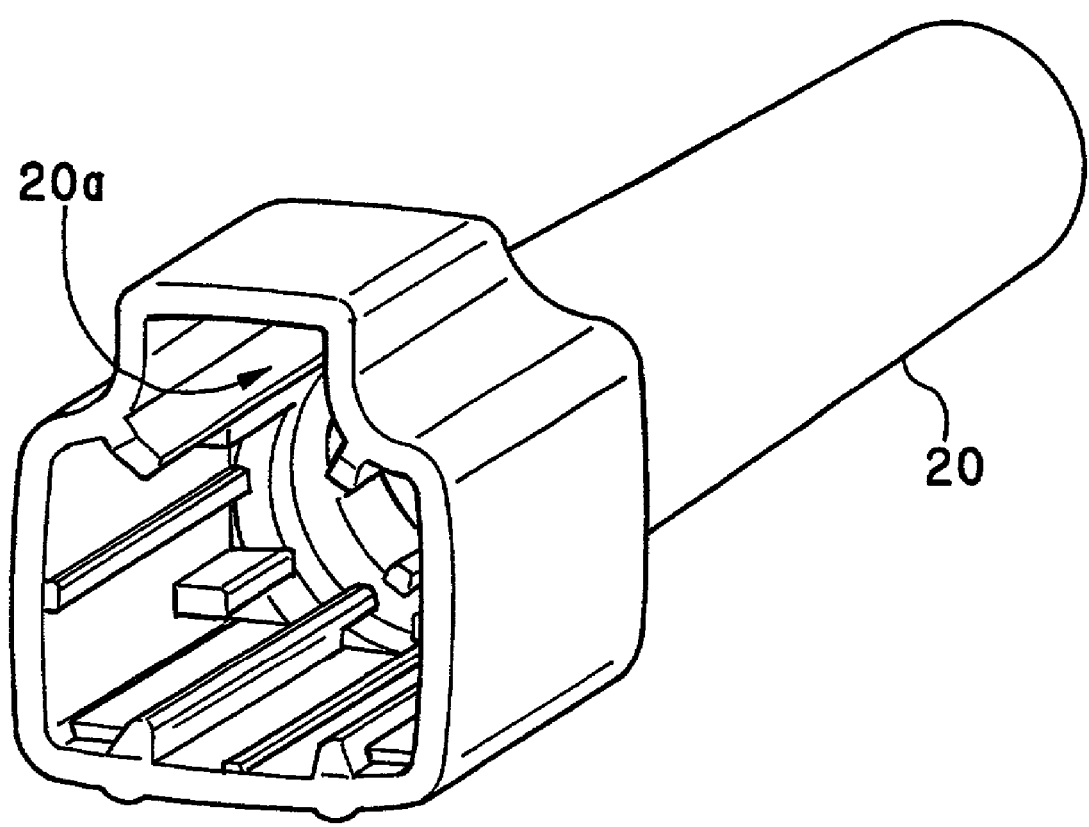
FIG. 8 is a perspective view showing a cap viewed from the opening side.

FIG. 7 shows a state where a cap 20 is fitted. FIG. 8 is a perspective view of cap 20 viewed from the opening side. Cap 20 covers outer and inner needles 11 and 12 in such a manner that they are ready for puncture and has an actuation stopper groove 20a in which actuating portion 6a is fitted in an immovable manner in order to make actuating portion 6a disabled. Hence, since actuating portion 6a is made disabled as long as cap 20 is fitted, it is possible to prevent inner needle 12 from being retracted into holder sleeve 1 as well as preventing other mal-operations.

The present invention will be described with reference to another embodiment with its drawings.

Figure 14:
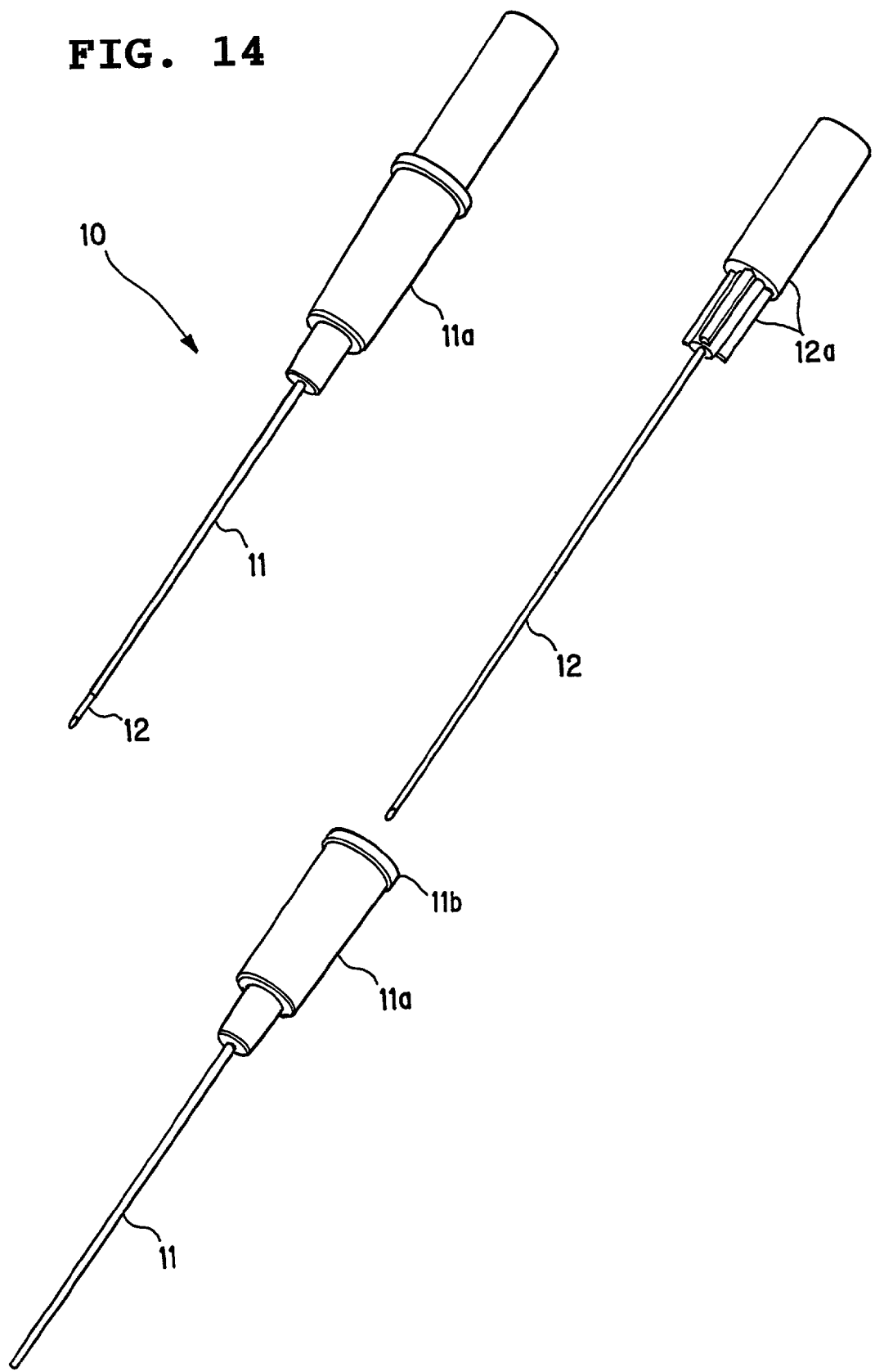
FIG. 14 is a perspective view showing a state where inner and outer needles are assembled.

The relationship between inner needle 12 and outer needle 11 is as shown in FIG. 14. As stated already, an outer needle structure 10 has outer needle 11 as a soft-resin made pipe needle. This outer needle 11 has a thin-walled pointed part producing an increased contact with inner needle 12. Provided at the side opposite to the pointed part is a funnel-shaped outer needle hub 11a for connection with a tube of a medical fluid such as for infusion.

Holder sleeve 1 has a slit 2 formed for assuring the path of movement of an actuator 6 when the retracting mechanism is actuated.

Figure 9:
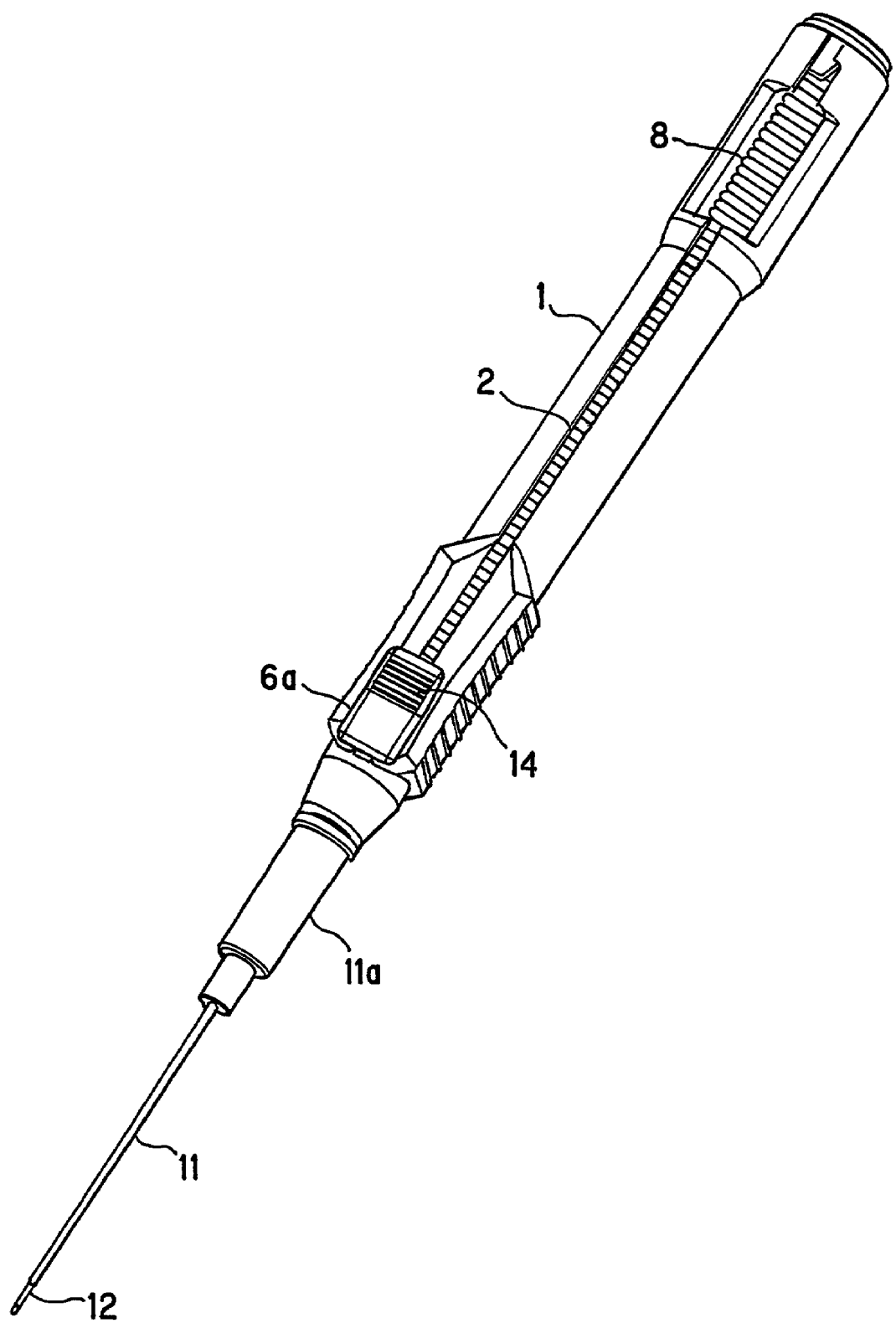
FIG. 9 is a perspective view showing the second embodiment.
Figure 10:
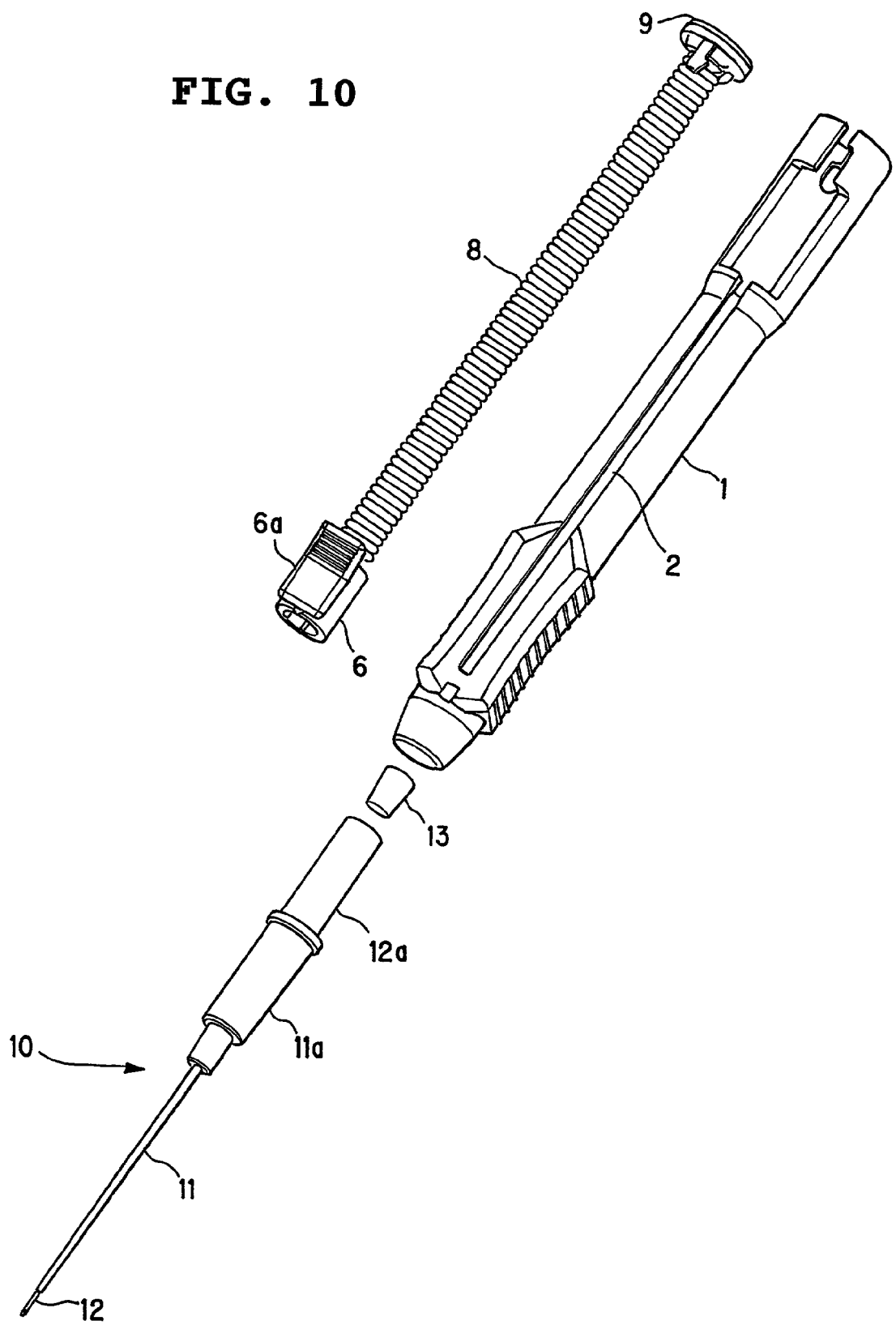
FIG. 10 is a partially exploded perspective view showing the second embodiment.
Figure 11:
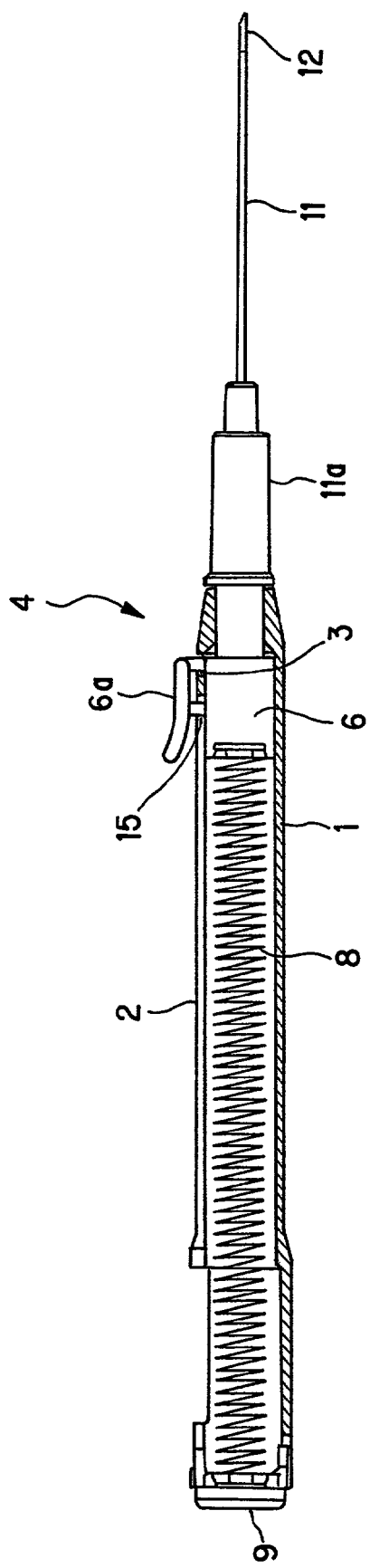
FIG. 11 a partially sectional view showing the second embodiment.

As shown in FIGS. 9 and 11, actuating portion 6a is extended from actuator 6 outwardly beyond the holder sleeve through slit 2 while the front part of actuating portion 6a is fitted into an engagement window 3 which is formed close to slit 2 in the front part of holder sleeve 1. This actuating portion 6a is also extended to the rear. When part of this actuating portion 6a extended to the rear is pressed, the insertion of the actuating portion into engagement window 3 is disengaged by the lever principle to reach the separated position. The actuating element has anti-slip ribs 14 at its rear part.

When inner and outer needles 12 and 11 are used to puncture, actuating portion 6a is positioned at the fitted position or fixed position 4 (FIG. 11) where the front part of actuating portion 6a is fitted in the engagement window 3 of holder sleeve 1. Therefore, outer and inner needles 11 and 12 are kept projected from the holder sleeve 1.

Figure 12:
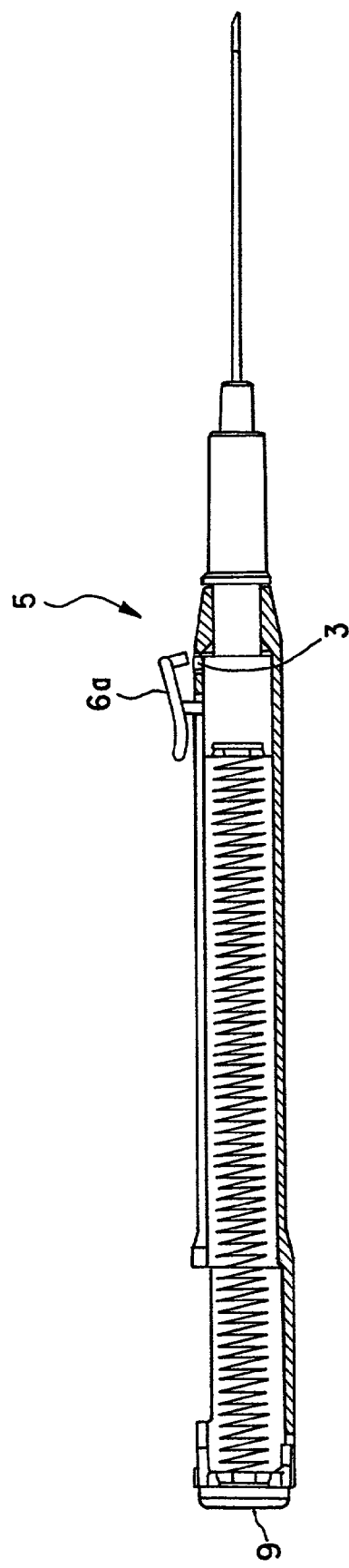
FIG. 12 a partially sectional view showing the second embodiment.
Figure 13:
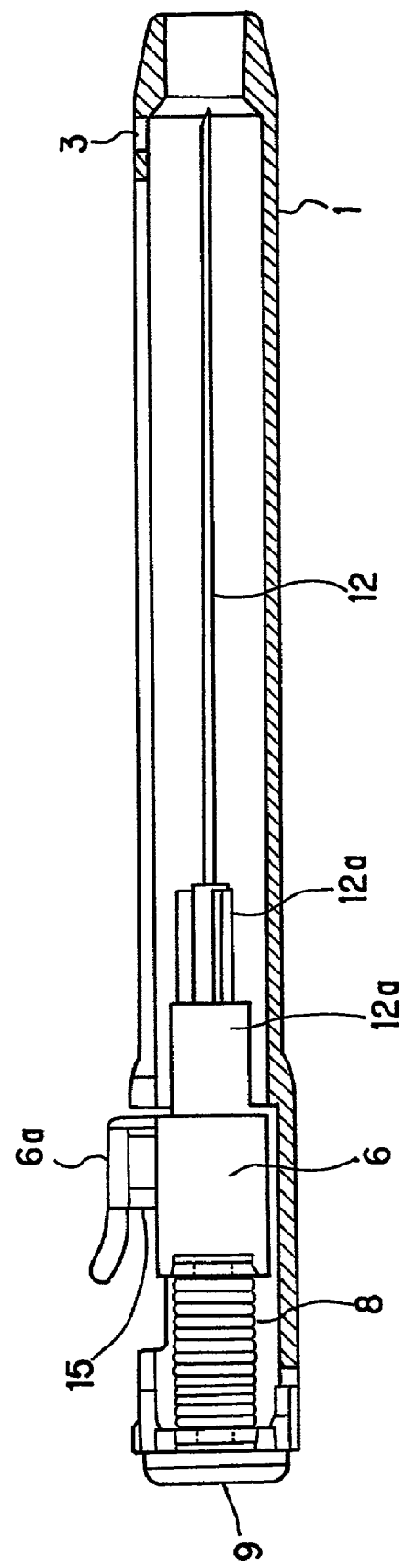
FIG. 13 is a partially sectional view showing a state where the inner needle is held in the second embodiment.

FIG. 13 shows the state of inner needle 11 and actuator 6 immediately after retraction. When the rear part of actuating portion 6a is pressed in the radial direction of holder sleeve 1, the front end of actuating portion 6a moves in the direction opposite to the pressed direction. Pressing the rear part of actuating portion 6a in the radial direction makes the front part of actuating portion 6a move to the position where the engaged state is released or a separated position 5 (FIG. 12). At the same time, the urging means urges inner needle 12 toward the rear end of holder sleeve 1 in direction of its axis, whereby actuator 6 smoothly and quickly moves to the rear side along the inner wall of the holder sleeve. In this way, inner needle 12 moves into the interior space of holder sleeve 1 and is stored therein as shown in FIG. 13.

With concern to the method of assembly of the safety indwelling needle of the present invention, actuator 6, coil spring 8 and tail plug 9 are inserted into holder sleeve 1 from its rear end. Actuator 6 is moved to the front of the holder sleeve with actuating portion 6a fitted through slit 2 until actuating portion 6a is inserted into engagement window 3. After the insertion, outer and inner needles 11 and 12 are attached to actuator 6 from the front side of the holder sleeve.

By adopting this method, assembly can be done without the needle tip being interfered since inner and outer needles 12 and 11 are not passed through either coil spring 8 or the holder sleeve. In view of improving the efficiency for fitting actuator 6, coil spring 8 and tail plug 9 from the rear end of holder sleeve 1, it is preferred that these three parts have been assembled in advance.

Figure 15:
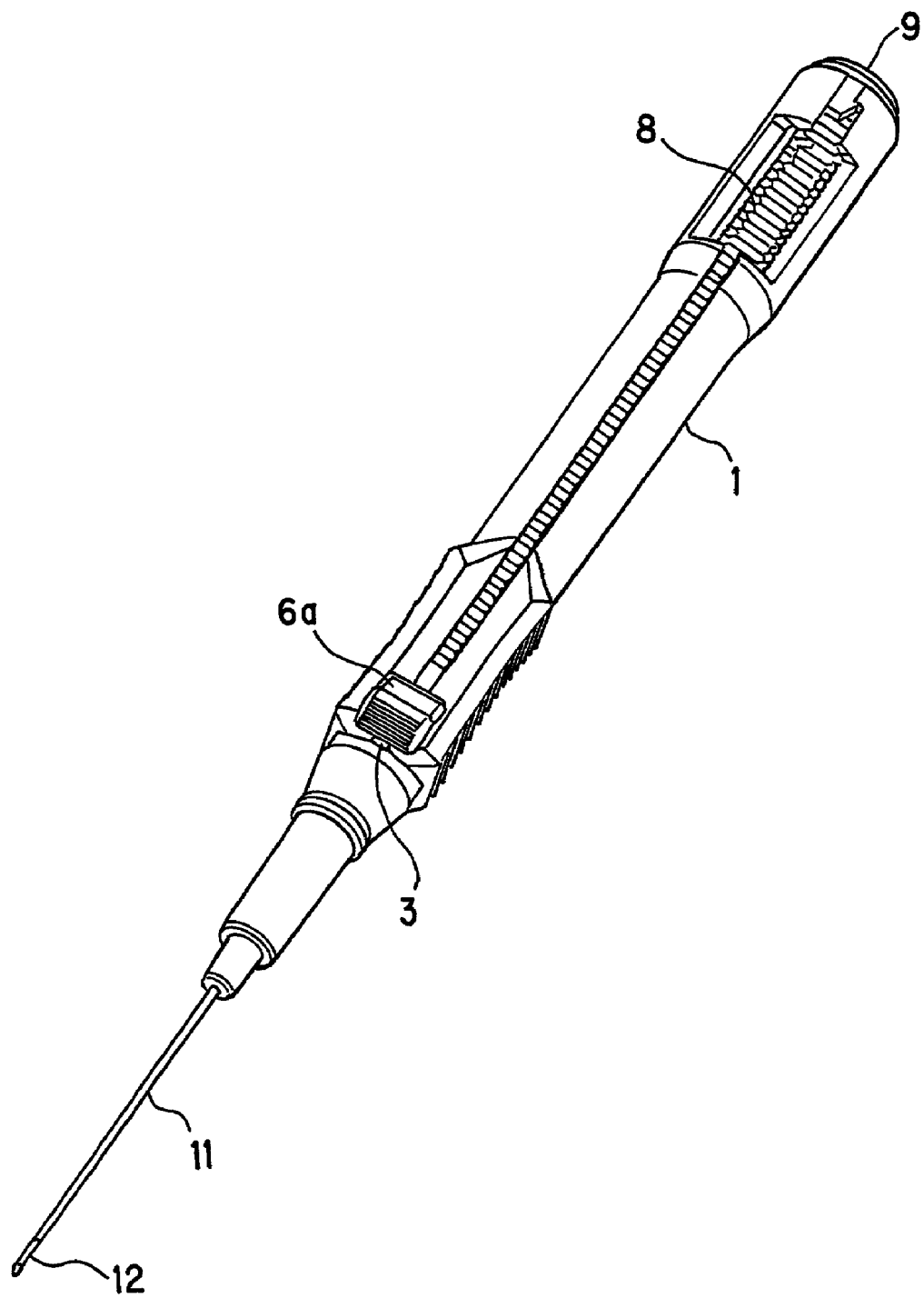
FIG. 15 is a perspective view showing the third embodiment.
Figure 16:
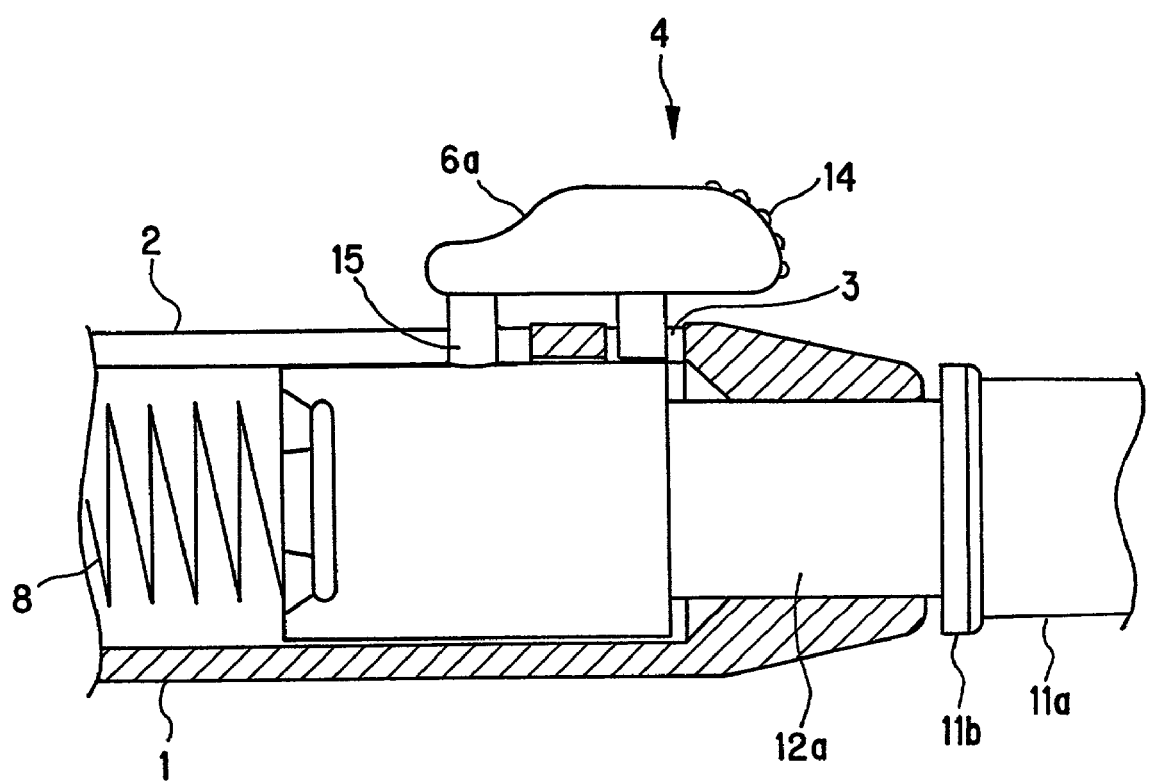
FIG. 16 is a partially sectional enlarged view showing an actuating portion and thereabout according to the third embodiment.
Figure 17:
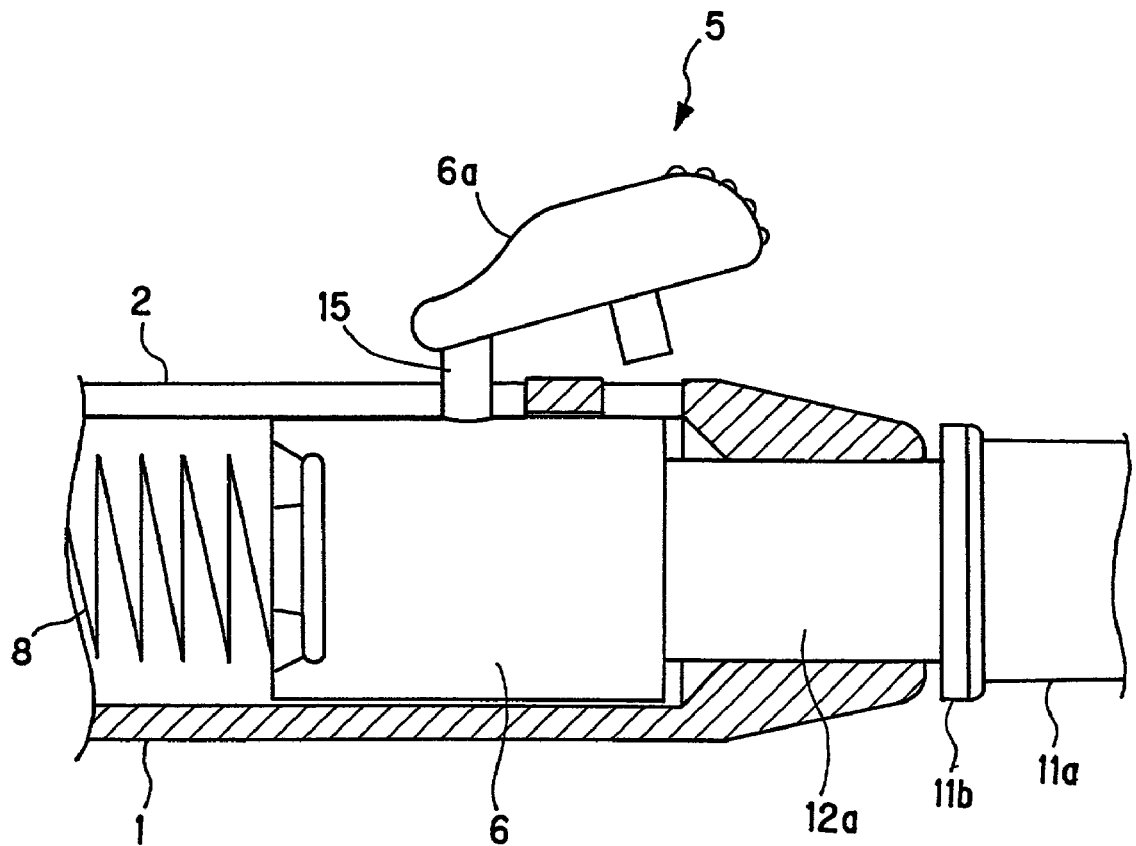
FIG. 17 is a partially sectional enlarged view showing an actuating portion and thereabout according to the third embodiment.

FIGS. 15 to 17 show a safety indwelling needle of the third embodiment. Actuating portion 6a shown in FIG. 15 is projected from actuator 6 through slit 2 and extended forwards only with part of it fitted in engagement window 3 of holder sleeve 1, as shown in FIG. 16. Anti-slip ribs 14 are formed on the front side surface of actuating portion 6a.

FIG. 17 shows the released state where the insertion of actuating portion 6a is disengaged. Shift of actuating portion 6a from its inserted state to released state is made by lifting the front part of actuating portion 6a where anti-slip ribs 14 are formed.

Even if the fingers of the health care worker or certain items present around the health care worker abut actuating portion 6a when inner and outer needles 12 and 11 is used to puncture, the moment of the force due to the abutment is opposite to the moment of a force for releasing the inserted state. Therefore, the moments of the force about the fulcrum at the joint 15 between the actuating element and the actuator act in the opposite direction mutually, so that the inserted state will not be released by an erroneous operation. The method of assembly and other configurations are the same as those shown in the embodiment described above.

Though this reference is common to other embodiments, it is preferred that actuator 6 and actuating portion 6a should be formed of a material having elasticity. This feature makes actuating portion 6a displace easily hence release easily from the inserted state. It is also possible to connect actuating portion 6a and actuator 6 with another element or configure part of actuating portion 6a to be fitted into engagement window 3, by a separate part.

Figure 18:
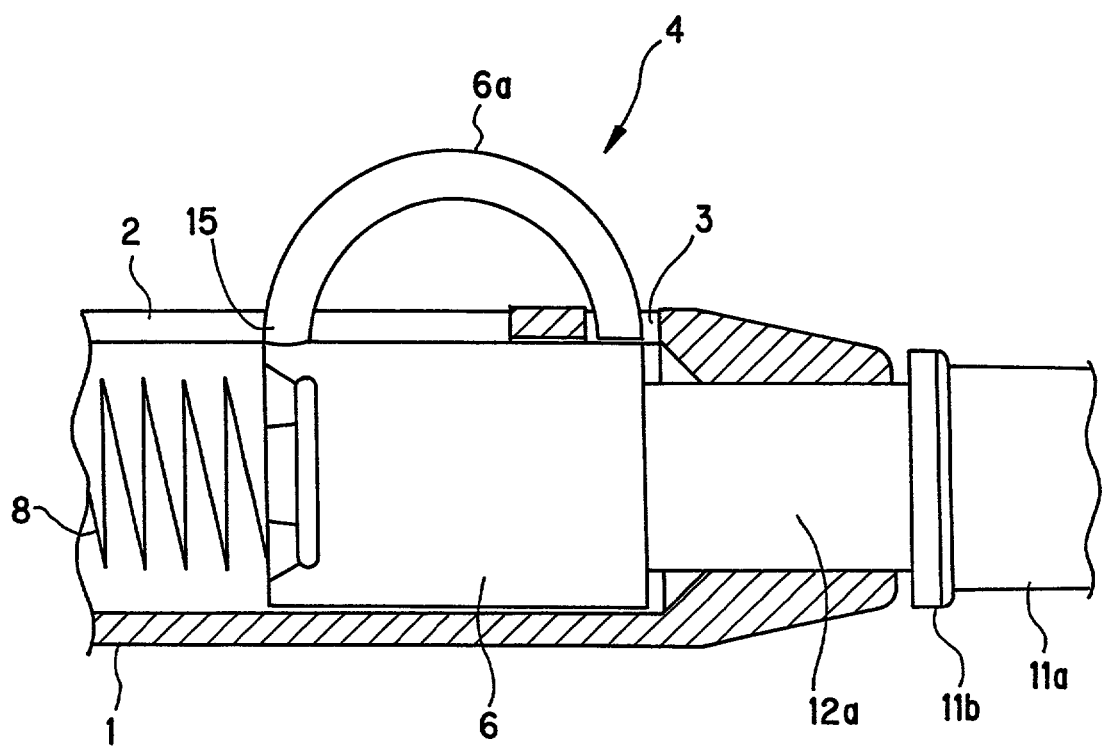
FIG. 18 is a partially sectional enlarged view showing an actuating portion and thereabout according to the fourth embodiment.
Figure 19:
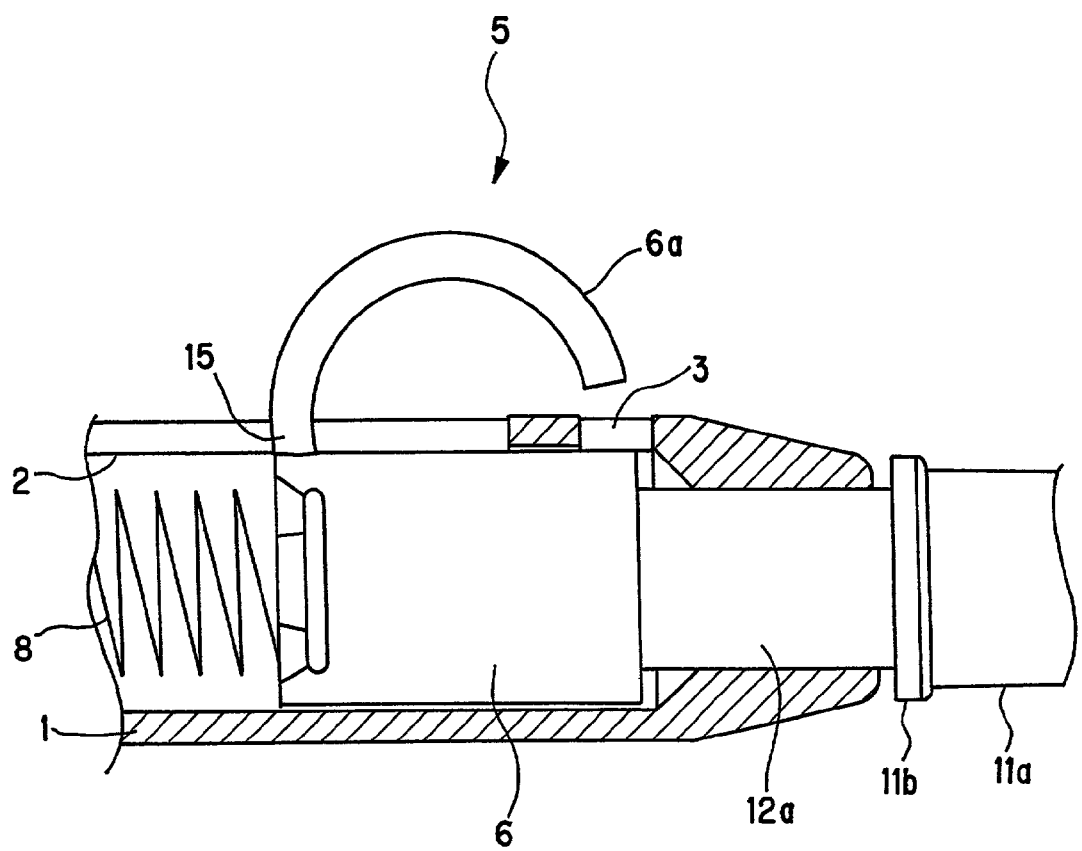
FIG. 19 is a partially sectional enlarged view showing an actuating portion and thereabout according to the fourth embodiment.

FIGS. 18 and 19 show the fourth embodiment of actuating portion 6a. FIG. 18 shows a state where the front part of actuating portion 6a fits into engagement window 3. In this state inner and outer needles 12 and 11 are used to puncture. FIG. 19 shows a state where the inserted state is disengaged. The inserted state is released by pressing actuating portion 6a from the holder sleeve side so as to lift actuating portion 6a. In this embodiment, other configurations are the same as those shown in the first embodiment.

In any of the above embodiments, an anti-slip portion such as anti-slip ribs 14 or a projection to be held by the finger may be formed on the actuating element in order to facilitate the actuating element to be handled.

It should be noted that the engaged state in the puncture position engagement portion can be disengaged by moving part of the actuating portion away from the holder sleeve. It is preferred that the path of movement of the actuating portion is included in the same plane that includes the axis of the holder sleeve.

Examples of the structures for releasing the engaged state by shifting part of the actuating portion away from the holder sleeve include a structure for directly lifting actuating portion 6a so as to move the engaging part away from the holder sleeve 1 side, and a structure in which, though actuating portion 6a is pressed toward holder sleeve 1, the engaging portion is lifted up by providing a pivot. As part of actuating portion 6a is moved away from holder sleeve 1, the engaged state of the puncture position engagement portion is released, whereby inner needle 12 is withdrawn into holder sleeve 1. This action, differing from a depressing action, almost never causes an erroneous actuation. Since the movement path of actuation is included within the same plane that includes the axis of holder sleeve 1, it is possible to provide a user-friendly safety indwelling needle, whether the user is left-handed or right-handed.

Also, the puncture position engagement portion of the safety indwelling needle may be constructed of an engagement window formed in the front part of the holder sleeve and an insert projection formed in the actuating portion, wherein the insert projection is fitted in the engagement window when in the puncture position and the engaged state can be released by moving the insert projection away from the holder sleeve. Also in this case, the action, differing from an depressing action, almost never causes an erroneous actuation. Further, also in this case, the movement path of actuation is included within the same plane that includes the axis of holder sleeve 1, it is possible to provide a user-friendly safety indwelling needle, whether the user is left-handed or right-handed.

Alternatively, the puncture position engagement portion of the safety indwelling needle may be formed of an engagement window formed in the front part of the holder sleeve and an insert projection formed in the actuating portion and constructed such that the insert projection is fitted in the engagement window when in the puncture position while the actuating portion is joined to the actuator at a position behind the insert projection, by an actuation support and the engaged state can be released by moving the insert projection away from the holder sleeve, by lifting the front part of the actuating portion.

In this case, the arrangement of the actuation support as the joint between the actuating portion and the actuator at a position behind the insert projection facilitates smooth actuation. Illustratively, when the inner needle is placed into the human body, the inner needle needs to be pushed out by the second digit. Hence, the second digit will be located around the cutout portion of the holder sleeve after the placement of the inner needle. Then, the withdrawal of the inner needle should follow. Since the actuating portion is joined to the actuator by the actuation support at a position behind the insert projection, the front part of the actuating portion should be pulled up in order to lift the insert projection. Therefore, the second digit is located around the cutout portion or in front of the actuating portion as mentioned above, this makes it possible to raise the front part of the actuating portion immediately, hence quickly begin to withdraw the inner needle. Further, a lifting portion which is touched by the finger when the insert projection is lifted from the engagement window may be formed at the front part of the actuating portion.

If no lift portion for raising the actuating portion is equipped, this makes quick withdrawal of the inner needle difficult. This is why a lifting portion is provided at the front part of the actuating portion in the present invention, whereby a quicker and more reliable retraction of the inner needle can be made possible.

It is preferred that the lifting portion is formed on the surface facing to the front as is shown in FIG. 6. It is also preferred that the angle a between the axis and the lifting portion is set at 90 degrees or smaller because this makes it possible for the lifting portion to hook the finger reliably. Moreover, it is preferred that anti-slip such as serration is formed because this also enables quick reliable withdrawal of the inner needle.

The safety indwelling needle of the present application is aimed at providing a technology which allows for easy assembly and prevention against re-exposure of the inner needle due to an external force.

In particular, a further object of the inventions written in the first to fifth aspects is to provide a safety indwelling needle which is able to prevent re-exposure of the inner needle due to an external force.

INDUSTRIAL APPLICABILITY

The safety indwelling needle according to the present invention is a safety indwelling needle comprised of a soft outer needle to be placed in a blood vessel and a hard inner needle which is fitted in the outer needle to pierce through the skin of a patient so as to insert the outer needle into a blood vessel, and provides a suitable configuration which prevents occurrence of erroneous operations before and during usage, is not different in handling depending on the handedness, allows for easy assembly and prevents re-exposure of the inner needle.

What is claimed is:

1. A safety indwelling needle, comprised of a metallic inner needle which pierces a skin of a patient and reaches a blood vessel; and a soft outer needle which is located outside the inner needle and places within the blood vessel, comprising:

a holder sleeve having a retracting mechanism which can hold the inner needle after a puncture, from a proximal end to a distal end thereof and does not hold the outer needle, characterized in that the retracting mechanism includes: an urging means for urging the inner needle to a side opposite to the outer needle with respect to an axial direction of the holder sleeve; an actuator which moves together with the inner needle when it is withdrawn and has a puncture position retainer for keeping the inner and outer needles ready for the puncture and an inner needle retraction actuating portion for allowing for the retraction actuation of the inner needle; and a slit formed in the holder sleeve for assuring a movement path of the actuator, the urging means is a biasing element that applies a biasing force to the actuator, the inner needle retraction actuating portion is positioned at an outside of the holder sleeve through the slit when the inner and outer needles are readied for the puncture, the puncture position retainer has a puncture position engagement portion whereby the actuator is engaged with the holder sleeve at a position on an outer needle side, the inner needle retraction actuating portion has an actuating portion for releasing the actuator from an engaged state of the puncture position engagement portion into an urged state by the urging means, and the retracting mechanism has an actuating portion housing for enclosing the inner needle retraction actuating portion when the inner needle retraction actuating portion biasedly retracts within and underneath a protective cover portion of the actuating portion housing to prevent both ends of the actuator from being freely accessible resulting in the actuating portion housing preventing the inner needle retraction actuating portion from coming into contact with a hand after retraction of the inner needle.

2. The safety indwelling needle according to claim 1, wherein the actuator housing portion is constructed of wall portions formed standing at both sides of the slit in the holder sleeve on the side opposite to the outer needle and the protective cover portion joining the edges of the wall portions.

3. The safety indwelling needle according to claim 2, wherein the protective cover portion is formed so as to function as a tail plug for closing an opening of the holder sleeve on the side opposite to the outer needle.

4. The safety indwelling needle according to claim 1, wherein the retracting mechanism has a stopper for arresting the inner needle moved to the side of the holder sleeve opposite to the outer needle, the stopper includes arrest engagements for stopping the inner needle stored in the holder sleeve relative to the holder sleeve.

5. The safety indwelling needle according to claim 1, wherein, on the outer needle side of the holder sleeve, a grip portion to be held when the outer and inner needles are punctured into the skin of the patient is formed at a position other than a position where the actuating portion of the actuator is arranged.

6. The safety indwelling needle according to claim 1, further comprising a cap which covers the outer and inner needles while keeping them ready for puncture and disables the function of the actuating portion.

7. A safety indwelling needle, comprised of a metallic inner needle which pierces a skin of a patient and reaches a blood vessel; and a soft outer needle which is located outside the inner needle and placed within the blood vessel, comprising:

a holder sleeve having a retracting mechanism which can hold the inner needle after a puncture, from a proximal end to a distal end thereof and does not hold the outer needle, characterized in that the retracting mechanism includes: a coil spring for urging the inner needle to a side opposite to the outer needle with respect to an axial direction of the holder sleeve; an actuator which is arranged between the coil spring and the inner needle, moves together with the inner needle when it is withdrawn and has a puncture position retainer for keeping the inner and outer needles ready for the puncture and an inner needle retraction actuating portion for allowing a withdrawal actuation of the inner needle; a slit formed in the holder sleeve for assuring a movement path of the actuator; an actuating portion housing for enclosing the inner needle retraction actuating portion when the inner needle retraction actuating portion biasedly retracts within and underneath a protective cover portion of the actuating portion housing to prevent both ends of the actuator from being freely accessible resulting in the actuating portion housing preventing the inner needle retraction actuating portion from coming into contact with a hand after retraction of the inner needle; and a stopper for stopping the inner needle, having been moved to a rear side with respect to the axial direction of the holder sleeve, the inner needle retraction actuating portion is positioned at an outside of the holder sleeve through the slit when the inner and outer needles are readied for the puncture, the puncture position retainer has a puncture position engagement portion whereby the actuator is engaged with the holder sleeve at a position on an outer needle side and an engaged state can be released, the inner needle retraction actuating portion includes: an actuating portion for releasing the actuator from the engaged state of the puncture position engagement portion into an urged state by the coil spring, the actuator housing portion is constructed of wall portions standing at both sides of the slit in the holder sleeve on the side opposite to the outer needle and a protective cover portion joining the edges of the wall portions, the protective cover portion being formed so as to function as a tail plug for closing an opening of the holder sleeve on the side opposite to the outer needle, and the stopper includes arrest engagements for stopping the inner needle held in the holder sleeve relative to the holder sleeve.

8. The safety indwelling needle according to claim 1, wherein the puncture position retainer is projected outward of holder sleeve through the slit, and the puncture position engagement portion is engaged with an engagement window provided on an outer surface of the holder sleeve.

9. The safety indwelling needle according to claim 7, wherein the puncture position retainer is projected outward of holder sleeve through the slit, and the puncture position engagement portion is engaged with an engagement window provided on an outer surface of the holder sleeve.

10. The safety indwelling needle according to claim 1, wherein the biasing element is in a compressed state when the inner needle is retracted.

11. The safety indwelling needle according to claim 7, wherein the coil spring is in a compressed state when the inner needle is retracted.

12. The safety indwelling needle according to claim 1, wherein the protective cover portion has a length that is greater than the length of the inner needle retraction actuating portion such that a free end of the protective cover portion extends beyond the inner needle retraction actuating portion so as to completely cover the inner needle retraction actuating portion.

13. The safety indwelling needle according to claim 1, wherein the housing is constructed such that lateral access to and access to the inner needle retraction actuating portion from above are prevented.

14. The safety indwelling needle according to claim 1, wherein the protective cover portion extends above and across a length of an outer surface of the holder sleeve.

15. A safety indwelling needle, comprised of a metallic inner needle which pierces a skin of a patient and reaches a blood vessel; and a soft outer needle which is located outside the inner needle and places within the blood vessel, comprising:

a holder sleeve having a retracting mechanism which can hold the inner needle after a puncture, from a proximal end to a distal end thereof and does not hold the outer needle, characterized in that the retracting mechanism includes: an urging means for urging the inner needle to a side opposite to the outer needle with respect to an axial direction of the holder sleeve; an actuator which moves together with the inner needle when it is withdrawn and has a puncture position retainer for keeping the inner and outer needles ready for the puncture and an inner needle retraction actuating portion for allowing for the retraction actuation of the inner needle; and a slit formed in the holder sleeve for assuring a movement path of the actuator, the urging means is a biasing element that applies a biasing force to the actuator, the inner needle retraction actuating portion is positioned at an outside of the holder sleeve through the slit when the inner and outer needles are readied for the puncture, the puncture position retainer has a puncture position engagement portion whereby the actuator is engaged with the holder sleeve at a position on an outer needle side, the inner needle retraction actuating portion has an actuating portion for releasing the actuator from an engaged state of the puncture position engagement portion into an urged state by the urging means, and the retracting mechanism has an actuating portion housing that includes a structure that extends the length of the inner needle retraction actuating portion when the inner needle retraction actuating portion retracts within the actuating portion housing such that a free end of the structure extends beyond the inner needle retraction actuating portion so as to completely cover the inner needle retraction actuating portion, thereby preventing the inner needle retraction actuating portion from coming into contact with a hand after retraction of the inner needle.

* * * * *